United States Patent [19]

Timpl et al.

US005177020A

[11] Patent Number: 5,177,020
[45] Date of Patent: Jan. 5, 1993

[54] METHOD FOR THE IMMUNOLOGICAL DETERMINATION OF HEPARAN SULFATE-PROTEOGLYCAN AND PROCESS FOR THE PREPARATION AND PURIFICATION OF HEPARAN SULFATE-PROTEOGLYCAN SUITABLE FOR THIS PURPOSE FROM TISSUES CONTAINING BASAL MEMBRANE

[75] Inventors: Rupert Timpl, Gauting; Mats Paulsson, Martinsried; Dietrich Brocks, Wiesbaden, all of Fed. Rep. of Germany

[73] Assignee: Hoechst Aktiengesellschaft, Frankfurt, Fed. Rep. of Germany

[21] Appl. No.: 563,803

[22] Filed: Aug. 6, 1990

Related U.S. Application Data

[63] Continuation of Ser. No. 331,048, Mar. 28, 1989, abandoned, which is a continuation of Ser. No. 844,372, Mar. 26, 1986, abandoned.

[30] Foreign Application Priority Data

Mar. 28, 1985 [DE] Fed. Rep. of Germany ....... 3511199

[51] Int. Cl.$^5$ ................. G01N 33/566; G01N 33/544; A61K 37/12; C07K 3/00
[52] U.S. Cl. ................... 436/501; 436/528; 436/815; 530/353; 530/387.1; 530/387.5; 435/7.1; 435/7.92; 435/7.93; 435/7.95
[58] Field of Search ............. 435/7.1, 7.92, 7.93, 435/7.95; 436/501, 528, 531, 815; 530/395, 353, 382.1, 387.5

[56] References Cited

U.S. PATENT DOCUMENTS

| 4,340,581 | 7/1982 | Timpl . | |
|---|---|---|---|
| 4,492,751 | 1/1985 | Boguslaski et al. | 436/817 X |
| 4,565,789 | 1/1986 | Liotta et al. | 436/808 X |
| 4,945,086 | 7/1990 | Benitz et al. | 514/56 |

OTHER PUBLICATIONS

Oohura et al. (1983) J. Biol. Chem. 258:2014-2021.
Dzadek et al. (Apr. 1985) EMBOJ 4:905-912.
Tyree et al., (Jun. 1984) Arch. Biochem Biophys 231:328-335.
Fujiwara et al., Chem. Abst. 101:1528 1c (No. 15, pp. 267-268) (1984).
Stow et al., Proc. Natl. Acad. Sci., 82:3296-3300 (May 1985).
Selden et al., Chem. Abst. 103:1742-45 U (No. 21, p. 301) (Nov. 25, 1985).
Mynderse et al., Laboratory Investigation, 48 (No. 3):292-302 (1983) (Nov. 25, 1985)
Paulsson et al., J. Mol. Bio. 197:297-313 (1987).

*Primary Examiner*—Christine M. Nucker
*Assistant Examiner*—David R. Preston
*Attorney, Agent, or Firm*—Finnegan, Henderson, Farabow, Garrett and Dunner

[57] ABSTRACT

The invention relates to a method for the immunological determination of basal membrane low-density heparan sulfate-proteoglycan in body fluids, and to the preparation or obtaining of a low-density heparan sulfate-proteoglycan suitable for this purpose, and of the corresponding highly specific antibodies.

12 Claims, No Drawings

METHOD FOR THE IMMUNOLOGICAL DETERMINATION OF HEPARAN SULFATE-PROTEOGLYCAN AND PROCESS FOR THE PREPARATION AND PURIFICATION OF HEPARAN SULFATE-PROTEOGLYCAN SUITABLE FOR THIS PURPOSE FROM TISSUES CONTAINING BASAL MEMBRANE

This application is a continuation of application Ser. No. 07/331,048 filed Mar. 28, 1989, now abandoned, which is a continuation of application Ser. No. 06/844,372, filed Mar. 26, 1986, now abandoned.

Heparan sulfate-proteoglycan occurs in basal membranes and acts there as an ion-selective filter. A diminution in this proteoglycan in basal membranes has been described in pathological situations such as, for example, diabetes mellitus. This diminution is regarded as being causally connected with the occurrence of late complications of diabetes, such as nephropathy. A tissue extraction, and thus the availability of tissue, is a prerequisite for the methods used to detect the diminution. It would be desirable to be able to determine such a change by an analysis of serum.

It has now been found, surprisingly, that low-density heparan sulfate-proteoglycan can be isolated pure from tissue containing basal membrane by use of the process according to the invention. Using this antigen and the corresponding highly specific antibodies it is possible to construct a highly sensitive immunological determination method. It is possible using this determination method according to the invention to detect even small amounts (ng/ml) of low-density heparan sulfate-proteoglycan in body fluids, in particular in blood or in serum.

This signifies a valuable extension of the methods of diagnosis. The concentrations of low-density heparan sulfate-proteoglycan normally found in the serum of normal individuals are in the range 100-150 ng/ml. There is a statistically significant increase in this concentration when there are changes to basal membranes such as, for example, in experimentally induced diabetes mellitus. It is now possible rapidly and reliably to detect such changes by use of the method according to the invention.

The invention relates to:

a) A process for the preparation of low-density ($\rho = 1.33-1.39$) heparan sulfate-proteoglycan, which comprises homogenization of basal membrane tissue in the presence of protease inhibitors, and extraction of heparan sulfate-proteoglycan from the tissue residue and purification by ion exchange chromatography followed by molecular sieve chromatography and fractionation in a density gradient, and the product which can thus be obtained.

b) A process for the production of a serum containing highly specific antibodies against heparan sulfate-proteoglycan, which comprises immunization of experimental animals with low-density heparan sulfate-proteoglycan, and obtaining their serum, and the product which can thus be obtained.

c) A method for the immunological determination of heparan sulfate-proteoglycan, which comprises determination of the antigen low-density heparan sulfate-proteoglycan and/or of its antigenic determinants in the body fluid.

The points listed are illustrated in detail in the description which follows and are defined in the claims.

In principle, the low-density heparan sulfate-proteoglycan can be obtained from all tissues containing basal membrane using the process according to the invention. The pure preparation of basal membranes is completely dispensed with in this process. Depending on the nature of the tissue, the isolation of the antigen is carried out directly using high concentrations of chaotropic salt solutions, or after removal of interfering proteins, which can be extracted with alkali metal salts.

Examples of suitable chaotropic salts are potassium thiocyanate, guanidinium thiocyanate and guanidinium chloride. Guanidinium chloride is preferably used. These salts are used in concentrations of 1-8 molar, the preferred range being 4 to 7 molar.

In the case of preextraction to remove interfering proteins, there are several possibilities depending on the contamination:

1. The tissue is comminuted and homogenized in aqueous buffer solution containing concentrations of alkali metal salts at a level such that no tissue constituents dissolve. NaCl or KCl are preferably used, in 3.4-4 molar concentration.
2. The process is carried out in the presence of low salt concentrations, preferably buffer solutions containing a 0.1-1 molar concentration of NaCl or KCl.
3. 1 and 2 are combined.

Following the preextraction, low-density heparan sulfate-proteoglycan is isolated as mentioned above. Both the actual extraction of the antigen and the prepurification are preferably carried out in the presence of protease inhibitors and at neutral pH.

Low-density heparan sulfate-proteoglycan is then purified from the extract by ion exchange chromatography, preferably on a weakly basic cation exchanger such as, for example, DEAE-cellulose or a DEAE-crosslinked dextran (for example Sephadex ®, Pharmacia Fine Chemicals Inc.) in the presence of high concentration of urea or its derivatives.

A first refining is carried out by molecular sieve chromatography. This results in a product of sufficient purity for the preparation of antibodies.

A subsequent density gradient centrifugation provides a low-density ($\rho = 1.33-1.39$ g/ml) heparan sulfate-proteoglycan which is free of proteins and nucleic acids.

The availability of a suitable antiserum against low-density heparan sulfate-proteoglycan is crucial for the determination method according to the invention. The antisera can be prepared in a customary manner by subcutaneous or intramuscular injection into experimental animals such as guineapigs, goats, sheep, donkeys and, preferably, rabbits. The presence of complete Freund's adjuvant is advantageous for this purpose. The antigen doses customary in these cases can be used. The preferred dose for rabbits is 0.5 to 1 mg per animal. The antiserum which has formed is then obtained in the manner known to the expert and can be used as such. It is also possible additionally to purify the antibodies present in the serum before their subsequent use. A preferred method for this is affinity chromatography, for example on affinity matrices to which the antigen has been covalently bonded, for example Sepharose ® activated with cyanogen bromide.

The labeling of the antigen, which is necessary for the immunological determination which is detailed below, can be carried out by the methods known for protein labeling. It is preferably radio-, enzyme- or fluorescence-labeled. In the case of radiolabeling, the radionuclide which is preferably used is iodine-125. It is then possible to carry out the labeling by the known chloramine T method (Int. Arch. Allergy 29, 185, 1966).

The low-density heparan sulfate-proteoglycan isolated by the abovementioned process according to the invention, and the antiserum, make it possible, as already mentioned, to carry out the determination, according to the invention, of low-density heparan sulfate-proteoglycan in body fluids, as well as of its antigenic determinants, in particular in serum, by use of immunological detection methods known per se.

It is possible to use for this method both the known radioimmunoassay (RIA) variants and the enzyme immunoassay variants and analogous determinations using other types of labeling, for example fluorescence-labeling, dyestuff-labeling and the like. Methods of these types are known to the expert, and it is not intended to detail them here.

In these detection reactions, there is competition, in a known manner, between the labeled low-density heparan sulfate-proteoglycan and unlabeled antigen, which is present in the sample to be determined, for the antibodies, so that the amount of labeled antigen in the antigen-antibody complex which is formed decreases as the amount of unlabeled antigens in the sample which is to be determined increases. It is possible to use either the labeling of the complex, for example the radioactivity or the enzyme activity, or the labeling of the supernatant after removal of the antigen-antibody complex, to establish, on the basis of a calibration curve drawn up using samples of known low-density heparan sulfate-proteoglycan content, the amounts of antigen contained in the sample under investigation. Preferably the labeling of the complex is determined.

A preferred embodiment of the immunological method according to the invention comprises removal of the antigen-antibody complex, which has formed with the specific antiserum, by use of a second antibody. An antibody directed against immunoglobulin G of the animal species used for obtaining the specific antiserum is preferably used for this. The removal of the antigen-antibody complex from the solution can be carried out by methods customary for this purpose, such as precipitation, centrifugation or filtration.

Alternatively, the antiserum or the second antibody is bound to a solid carrier. After removal of the antigen-antibody complex the radioactivity, or another labeling, contained in the complex or remaining in the solution is determined.

Another variant for the determination of low-density heparan sulfate-proteoglycan can also be carried out in such a manner that the antibody against immunoglobulin G of the relevant animal species, for example of rabbits, is labeled, the labelings which have already been detailed likewise being suitable, but enzyme labeling preferably being used. In an enzyme immunoassay, for example, the part of the anti-heparan sulfate-proteoglycan (low density) serum remaining after formation of the antigen-antibody complex is determined by binding the former to carrier-bound low-density heparan sulfate-proteoglycan and then reacting it with enzyme-labeled antibodies against rabbit immunoglobulin G. The amount of bound, enzyme-labeled antibody is then determined by measurement of the enzymatic reaction and is indirectly proportional to the unknown amount of low-density heparan sulfate-proteoglycan in the sample.

The examples which follow further illustrate the invention.

EXAMPLE 1

Preparation of low-density heparan sulfate-proteoglycan a) Human placenta is used as the starting material. The tissue is homogenized two or three times in an 20-fold excess of 0.15 M NaCl, 0.05 M tris.HCl (pH 7.4) in the presence of the protease inhibitors phenylmethanesulfonyl fluoride (PMSF) (2.5 mM), the mercury salt of p-chlorobenzoic acid (3 mg/ml), EDTA (10 mM) and N-ethylmaleimide (NEM) (2.5 mM), and extractable protein is removed by centrifugation.

The residue is then extracted twice with 6 M guanidinium chloride, 0.05 M tris.HCl, pH 7.4, in the presence of the protease inhibitors, at 4° C. The extract contains heparan sulfate-proteoglycan. Heparan sulfate-proteoglycan is further purified by ion exchange chromatography on DEAE cellulose which has been equilibrated with 7 M urea, 0.05 M tris.HCl (pH 8.6), 0.5 mM EDTA, 0.5 mM NEM, 0.5 mM PMSF at 4° C., and elution with a 0–0.6 M NaCl gradient, the product eluting in the second half of the gradient.

Following molecular sieve chromatography on an allyldextran crosslinked with N,N'-methylenebisacrylamide (for example Sephacryl ® S400, Pharmacia Fine Chemicals Inc.), equilibrated with 6 M guanidinium chloride, 0.05 M tris/HCl, pH 7.4, with the inhibitors used for the DEAE-cellulose chromatography, and CsCl density gradient centrifugation in 6 M guanidinium chloride buffer, with an initial density of 1.34 g/ml ($>100,000 \times g$, 8 h, 18° C.), the low-density heparan sulfate-proteoglycan obtained in the central portion of the gradient ($\rho = 1.33-1.39$ g/ml) is free of high-density heparan sulfate-proteoglycan, glycoproteins and nucleic acids.

b) The process is carried out as in 1a) when a mouse tumor [EHS sarcoma, described by Orkin et al., J. Exp. Med. 145, 204–220 (1977)] is used as starting material. However, prepurification to extract interfering proteins is unnecessary.

EXAMPLE 2

Preparation of the labeled antigen 25 ng of low-density heparan sulfate-proteoglycan are labeled with 0.5 mCi of iodine-125 by the chloramine T method, and unbound iodine is removed by dialysis or gel filtration on a polyacrylamide gel (for example Biogel ® P2, Pharmacia Fine Chemicals Inc.).

EXAMPLE 3

Procedure for the immunological determination (RIA)

All the steps necessary for the immunological determination are carried out in the presence of 0.04% of a non-ionic detergent such as, for example, Tween 20, a polyethoxylated sorbitol monolaurate. Binding plots are determined with 1 ng of labeled heparan sulfate-proteoglycan. The concentration of heparan sulfate-proteoglycan in an unknown sample of serum, or other body fluids, is determined in the following inhibition assay:

A defined amount of the specific antibody or antiserum is preincubated with the unknown sample at 4° C. for 16 h and, after addition of 1 ng of labeled antigen, incubation is continued at 4° C. for 8 hours. Then an excess of antibodies against rabbit immunoglobulin G is added and, after a further 16 h at 4° C., the antigen bound in the immune complex is removed by centrifugation. The inhibitory activity of the unknown sample is compared with the activity of a standard concentration of unlabeled antigen.

EXAMPLE 4

Preparation of the antiserum

Rabbits are immunized with 0.5–1 mg of low-density heparan sulfate-proteoglycan per animal, by subcutaneous or intramuscular injection of the antigen solution mixed with an equal volume of complete Freund's adjuvant. An equal amount of antigen solution mixed with complete Freund's adjuvant is injected subcutaneously or intramuscularly 4 weeks after the first injection. Blood is obtained 4 to 8 weeks after the 2nd injection, and the antiserum is obtained from it after coagulation.

We claim:

1. A process for the preparation of substantially pure low-density ($\delta = 1.33-1.39$) heparan sulfate-proteoglycan of about 620–680 kd, which comprises:
   a) extraction of basal membrane tissue from human placenta in the presence of protease inhibitors,
   b) extraction of said low-density heparan sulfate-proteoglycan from said extracted tissue into an aqueous phase with chaotropic salt, and
   c) purification of said low-density heparan sulfate-proteoglycan by ion exchange chromatography followed by molecular sieve chromatography and fractionation in a density gradient.

2. A method for the immunological determination of low-density heparan sulfate-proteoglycan antigen of approximately 620–680 kd from basal membrane tissue of human placenta, or its antigenic determinants in a sample of body fluids, comprising the steps of:
   a) reacting the sample of antigen or its antigenic determinants with an amount of antibodies specific to said antigen that is in excess quantity relative to the sample being investigated to form an antigen-antibody complex and unreacted antibodies; and
   b) determining the presence or amount of antigen in the sample by immunological methods.

3. The method of claim 2, wherein said determining step comprises performing a competition reaction between the antigen in the sample and labeled low-density heparan sulfate proteoglycan from basal membrane tissue of human placenta.

4. The method as claimed in claim 3, wherein the labeled antigen is radio-, enzyme- or fluorescence-labeled.

5. The method as claimed in claim 3, wherein the antigen-antibody complex is removed by a further step comprising the reaction of the antigen-antibody complex with a second antibody which is bound to a solid carrier.

6. The method of claim 2, wherein said determining step comprises:
   a) reacting the unreacted antibodies with low-density heparan sulfate-proteoglycan antigen from the basal membrane tissue of human placenta that is bound to a carrier to form a carrier-antigen-antibody complex;
   b) reacting said carrier-antigen-antibody complex with labeled second antibody which binds to said carrier-antigen-antibody complex to form a labeled complex;
   c) separating the labeled complex from supernatant containing unbound labeled second antibody; and
   d) measuring the amount of the labeled second antibody in the labeled complex or in the supernatant wherein the amount of labeled second antibody corresponds to the amount of said antigen or its antigenic determinants in said body fluids.

7. The method as claimed in claim 6, wherein the second, labeled, antibody is radio-, enzyme- or fluorescence-labeled.

8. Substantially pure low-density heparan sulfate-proteoglycan of about 620–680 kd from basal membrane tissue of human placenta ($\delta = 1.33-1.39$) which is substantially free of proteins and nucleic acids and which can be obtained by the process of claim 1.

9. A substantially pure antibody preparation specific for heparan sulfate-proteoglycan from immunized animals containing antibodies against low-density heparan sulfate-proteoglycan of about 620–680 kd ($\delta = 1.33—1.39$) extracted from basal membrane tissue.

10. Substantially pure low-density heparan sulfate-proteoglycan of about 620–680 kd from human placenta basal membrane tissue.

11. Substantially pure antibody specific to low-density heparan sulfate-proteoglycan of about 620–680 kd from human placenta basal membrane tissue.

12. A method for the detection of heparan sulfate-proteoglycan in a sample comprising the steps of:
   a) immunizing an animal with the low-density heparan sulfate-proteoglycan of claim 1,
   b) obtaining substantially pure antibody from the animal which is highly specific for low-density heparan sulfate-proteoglycan,
   c) incubating the antibody with said sample to allow formation of specific antigen-antibody complexes, and
   d) measuring said specific antigen-antibody complexes and determining if heparan sulfate-proteoglycan is present in said sample.

* * * * *